United States Patent
Struszcyk et al.

(10) Patent No.: US 6,740,752 B2
(45) Date of Patent: May 25, 2004

(54) PROCESS FOR PREPARING CHITOSAN PARTICLES

(75) Inventors: Henryk Struszcyk, Zgierz (PL);
Antoni Niekraszewicz, Lodz (PL);
Magdalena Kucharska, Lodz (PL);
Alojzy Urbanowski, Lodz (PL); Maria Wisniewska-Wrona, Lodz (PL)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/278,534

(22) Filed: Oct. 23, 2002

(65) Prior Publication Data

US 2003/0057159 A1 Mar. 27, 2003

Related U.S. Application Data

(63) Continuation of application No. PCT/US01/15182, filed on May 10, 2001.

(30) Foreign Application Priority Data

May 12, 2000 (PL) .................................................. 340132

(51) Int. Cl.$^7$ .............................. C08B 37/08; C08J 3/07; C08J 3/14
(52) U.S. Cl. ...................... 536/124; 536/1.11; 536/20; 536/55.2; 536/55.3; 536/123.1; 210/702
(58) Field of Search .................. 536/1.11, 20, 55.2, 536/55.3, 123.1, 124

(56) References Cited

U.S. PATENT DOCUMENTS 6,638,918 B2 * 10/2003 Davison et al. ............... 514/55

FOREIGN PATENT DOCUMENTS

| PL | 125995 | 5/1984 |
|---|---|---|
| PL | 164247 B1 | 7/1994 |
| WO | WO 91/00298 | 1/1991 |

OTHER PUBLICATIONS

Struszczyk, "Microcrystalline Chitosan. I. Preparation and Properties of Microcrystalline Chitosan," Journal of Applied Polymer Science, vol. 33 177–189 (1987).

* cited by examiner

Primary Examiner—Samuel Barts
Assistant Examiner—Ganapathy Krishnan
(74) Attorney, Agent, or Firm—Peter D. Meyer

(57) ABSTRACT

Disclosed is a process for producing particles of the modified carbohydrate polymer chitosan. Such chitosan particles are "activated" as a consequence of the specific steps used in the process. The process involves precipitation of dissolved chitosan from an acid solution thereof by the stepwise addition of neutralizing agent to the solution. A partial neutralization is carried out under shear agitation to form a continuous gel phase having a pH within the range of 5.0 to 6.9. This partially neutralized chitosan gel phase is then further subjected to shear agitation for at least 10 seconds to homogenize the gel phase. The homogenized gel phase is then further neutralized under shear agitation to a pH of above 6.9 to form a gel-like suspension of discrete chitosan particles. Chitosan particles in this form are useful in a number of contexts including, in particular, in the area of plant care.

21 Claims, No Drawings

PROCESS FOR PREPARING CHITOSAN PARTICLES

CROSS REFERENCE TO PRIOR APPLICATION

This is a continuation of International Application No. PCT/US01/15182, with an international filing date of May 10, 2001, and published in English.

TECHNICAL FIELD

The present invention relates to a process for preparing particles of chitosan. Chitosan particles in this form which are prepared according to the process herein are "activated" in the sense that they are especially useful for providing plant care benefits.

BACKGROUND OF THE INVENTION

Chitosan is a modified carbohydrate polymer derived from the chitin component of the shells of crustaceans such as crabs, shrimp and cuttlefish. Chitosan is used for a wide variety of purposes including plant care, cosmetics additives, food and nutrition supplements and medical care uses.

Both Polish Patent No. 125,995 and the periodical "Journal of Applied Polymer Science" Vol. 33 p. 177, 1987 disclose a method for producing a form of chitosan with a developed internal surface. This is done via a batch process in which the chitosan is periodically precipitated from its solutions in aqueous organic or inorganic acids or their salts by means of neutralization with hydroxides of alkali metals. The precipitation mixture is vigorously stirred. The precipitated chitosan in gel or suspension form is washed several times with water. This known method permits production of chitosan having a developed internal surface with a yield of 70–90% of theoretical. However, the procedure is a batch process which requires at least 12–24 hours for a production cycle. The single batches of the product are lacking homogeneity. The product has a distinct tendency toward degradation and its sorption capacity is rather poor resulting from the relatively low degree of development of the inner surface of the chitosan particles.

Polish Patent No. 164,247 and Finnish Patent No. 83,426 both disclose a continuous method for producing microcrystalline chitosan. In this method a solution of chitosan in aqueous acids and/or their salts is introduced to a reactor along with an aqueous solution of alkali metal hydroxides or salts. This results in formation of suspension of microcrystalline chitosan particles with a suspension pH>7. Simultaneously, this alkaline suspension of the formed microcrystalline chitosan particles is continuously removed from the reactor. The alkaline solution may also be introduced directly to a recirculation system. This method has several drawbacks including a yield below 90%, and realization of chitosan agglomerates with an average particle size above 1 $\mu$m and water retention value below 5000%. The water retention value is an indication of the development of the inner surface. Moreover, it is not possible to control the molecular, supermolecular and morphological structure of the chitosan particles produced. This continuous process also causes a substantial decrease of the average molecular weight of the generated microcrystalline chitosan as result of intensive degradation effects.

SUMMARY OF THE INVENTION

The present invention provides a process for preparing particles of "microcrystalline" chitosan in the form of an aqueous suspension of such particles. As a consequence of the specific steps used to carry out the process, the chitosan particles in the suspension are "activated" in the sense that the chitosan material in this form is especially useful for a number of purposes including in particular the provision of a variety of plant care benefits.

In the first step of the process herein, an aqueous solution is formed, generally containing at least 0.001% and preferably from 0.01% to 10.0% by weight of chitosan which can be provided by any conventional chitosan source. This solution contains organic or inorganic acids and/or salts of such acids in an amount sufficient to maintain the solution at a pH which is low enough to completely solubilize the chitosan.

In the next step of the process, the aqueous solution of the first step is partially neutralized by adding a neutralizing agent while subjecting the solution to shear agitation. The neutralizing agent addition and the agitation are sufficient to convert the solution into a continuous gel phase having a pH of from 5.0 to 6.9

In the next process step, the partially neutralized gel formed in the previous step is maintained under shear agitation for at least 10 seconds after the gel phase has been formed in order to homogenize the gel phase. This agitated homogenized gel is then further neutralized under continuing agitation by addition of more neutralizing agent sufficient to raise the pH within the homogenized gel phase to above 6.9, preferably above 7.3. Agitation is preferably continued for at least another 10 seconds after this elevated pH is reached. This then forms a gel-like suspension of discrete particles of activated microcrystalline chitosan having desirable properties.

In preferred embodiments of the present process, the aqueous solution formed in the initial step can be filtered prior to neutralization to remove insoluble matter such as may have been introduced with the chitosan source. Also preferably the chitosan particles of the eventually formed gel-like suspension may be washed, e.g., with water, to remove such materials such water soluble salts.

Preferably the chitosan particles produced by the process of this invention are characterized by having an average particle size of from 2 to 20 $\mu$m. Preferably also such particles further have a water solubility of at least 90% at pH 6 after 24 hours.

DETAILED DESCRIPTION OF THE INVENTION

In the first step of the process described above, an aqueous solution of chitosan is formed. This can be accomplished by combining chitosan with an aqueous solution containing organic or inorganic acids or their salts. Such acids can include, for example, acetic acid, lactic acid, salicylic acid, hydrochloric acid, and the like. Sufficient acid or salt thereof must be utilized to maintain this solution at a pH wherein the chitosan is essentially completely dissolved, i.e., solubilized. Agitation sufficient to facilitate chitosan dissolution may be utilized.

Any conventional source of chitosan may be utilized to form the chitosan solution. Such chitosan sources may be those derived from shellfish or may be fungally derived. Commercially available chitosan sources are marketed, for example, under the tradenames "Chitosan" by Vanson, Inc. of Redmond, Wash., USA and "Chitoclear" by Primex Ingredients SA of Avaldsnes, Norway.

The chitosan is utilized to an extent which is sufficient to form a concentration of chitosan in the aqueous solution of at least 0.001% by weight. More preferably, the solution will contain from 0.01% to 10.0% by weight, most preferably from 0.01% to 1.5% by weight.

After the aqueous chitosan solution has been formed in the first essential step of the process herein, such a solution may optionally be filtered before further processing in order to remove therefrom any insoluble material which might remain therein. Such insoluble material, for example, may have been introduced into the solution from the chitosan source.

In a second essential step of the process herein, the chitosan solution formed in the first essential process step is partially neutralized. This is accomplished by adding a neutralizing agent to the solution while maintaining the solution under shear agitation. Neutralization agents which can be used in this step include hydroxides such as sodium, potassium and ammonium hydroxides and their salts. Preferably these neutralization agents are combined with the first step chitosan solution in the form of aqueous solutions having a neutralizing agent concentration of from 0.01% to 20% by weight.

Partial neutralization in this second essential process step is effected while the combined chitosan/neutralizing agent solution is maintained under shear agitation. Both the addition of the neutralizing agent and the shear agitation should be sufficiently carried out in order to convert the solution into a continuous gel phase having a pH within the range of from 5.0 to 6.9. Typically shear agitation to the extent of from 10 to 1000 $\sec^{-1}$ (rpm) can be used.

After this continuous gel phase has been formed, the gel phase is next subjected to continued shear agitation in order to homogenize this gel phase. Generally such continued shear agitation is carried out for a period of at least 10 seconds and preferably for a period of from 1 to 60 minutes. Typically shear agitation utilized at this point is applied to the extent of from 100 to 5000 $\sec^{-1}$.

Next the homogenized gel phase from the previous step is further neutralized while still being subjected to shear agitation. In this step, neutralizing agent is added to the extent needed to raise the pH within the gel to above 6.9, and preferably to within the range of 7.1 to 7.5, e.g., above 7.3. This generally occurs under shear agitation of from 10 to 1000 $\sec^{-1}$. After the requisite pH is reached, high shear agitation (100 to 5000 $\sec^{-1}$) can be used to homogenize the suspension. The same type and form of neutralizing agents as specified above for the partial neutralization step can be utilized in this further neutralization step. Alternatively, the neutralizing agent used in this further neutralization step does not have to be identical to the neutralizing agent used in the partial neutralization step.

This further neutralization step produces a gel-like suspension of discrete particles of chitosan. Preferably this suspension of particles at this point can be washed, e.g., with water, to remove therefrom any residual soluble salt impurities. The chitosan particles in the suspension may also be concentrated, recovered and/or dried in conventional manner. The process of this invention may be carried out in either a batch-wise or continuous format.

In the process according to this invention, during the initial partial neutralization step, the sol form of the chitosan salt is transformed into gel. Simultaneously, nucleation points appear for the agglomerates of chitosan. Without being bound by theory, it is believed that the intensive agitation causes this. An agglomerate structure emerges and a physical-chemical modification of the initial gel form proceeds. Further on in the process during further neutralization, the final agglomerate structure of the chitosan particles forms. The stabilization of the agglomerates of the physical/chemical modified chitosan particles proceeds in the final step of the process. During this chitosan manufacturing procedure, a controlled structure of the product is formed with respect to the molecular, supermolecular and morphological characteristics of the resulting material.

The chitosan particles produced by this invention are characterized herein as "microcrystalline" even though their degree of crystallinity is very low, and, in fact is much lower than the degree of crystallinity of commercial chitosan products which have a significant crystalline content. Perhaps more accurately, the particles herein can be characterized as "activated" given their utility in a number of contexts as described hereinafter. The chitosan material of the particles which are produced has a modified specific molecular structure having specific molecular weight and degree of polydispersity. It also has a supermolecular structure having certain morphological characteristics which provide relatively high porosity and relatively high ability to retain water in a capillary system.

The modified chitosan can be prepared according to this invention with a yield of over 90%, usually 95–99.5%. The material is highly homogenous and well reproducible. It has average molecular weight which is close to that of the initial chitosan with lowered molecular polydispersity. The material also has a Water Retention Value (WRV) which is generally much higher than that for the starting chitosan. WRV will, in fact generally exceed 1000% and can even exceed 5000%, a value not attainable via previously known methods.

The process of the instant invention permits realization of activated chitosan with a modified structure, in the form of a gel-like suspension, paste or powder. The gel-like form is stable with attainable agglomerate sizes below 1 $\mu$m. Preferably, however, the average particle size of the chitosan particles in suspension will range from 2 to 20 $\mu$m. Preferably also these particles will have a water solubility of at least 90%, preferably 95%, at pH 6 after 24 hours.

The modified chitosan prepared according to the present invention can be applied in agriculture, medicine, pharmacy, veterinary medicine, chemical industry, health and beauty care products and environment protection. As indicated hereinbefore, the activated chitosan produced by this invention is particularly useful in the area of plant care.

The process of this invention, and the material produced thereby, are illustrated by following examples which do not limit the scope of the present invention.

EXAMPLE I 800 parts by weight of a 1% aqueous solution of commercially available chitosan (Primex Chitoclear) in 2% acetic acid are introduced to a reactor equipped with an agitator. The initial polymer is characterized by: average molecular weight $\overline{M}v$=550 kD, deacetylation degree DD=80.6%, polydispersity degree Pd=4.85, ash content 1.70%. At rotation speed 60 rpm of the agitator, a 1.5% aqueous solution of sodium hydroxide is introduced through a metering pump to achieve pH=6.85 which is the turning point of the chitosan salt mixture from the sol to gel form. The gel so obtained is agitated for 5 minutes at 1000 pm. Thereafter the neutralization is continued with addition of the 1.5% aqueous sodium hydroxide at agitation speed 4000 rpm during next 5 minutes to attain pH=7.5. Next the mixture is homogenized over 10 minutes. The chitosan obtained in a gel-like suspension is continuously washed with water. The suspension is next concentrated. 840 wt parts of chitosan are obtained in form of a white gel-like suspension with 0.94% concentration and with following characteristics: $\overline{M}v$=488.9 kD, DD=80.6%, WRV=4500%, Pd=4.45 and average size of the agglomerates 0.5 to 3 $\mu$m. Ash content is 0.32% wt.

EXAMPLE II

To a reactor, as in Example I, 1000 parts by wt are introduced of a 1% aqueous chitosan solution (with properties as in Example I) along with a 1.5% solution of lactic acid. With continual agitation at 120 rpm, a 0.75% aqueous solution of sodium hydroxide is continuously introduced through a metering pump to achieve pH 6.0–6.8. This results in the transformation of the chitosan salt from the sol form into gel and a partial formation of the chitosan form. The intermediate product obtained is homogenized for 1 minute at 1000 rpm followed further by 10 minutes of neutralization with the 0.75% aqueous sodium hydroxide solution at 4000 rpm to achieve pH=7.5. This is followed by 5 minutes of homogenizing. The chitosan obtained in a gel-like suspension is purified as in Example I.

In this case 640 parts by wt of chitosan are obtained in the form of a white gel-like suspension with 1.5% concentration of the polymer and following characteristics: $\overline{M}v$=491.5 kD, DD=80.6%, WRV=2300%, Pd=4.88, ash content 0.1% and average agglomerate size=0.5–5 $\mu$m

EXAMPLE III

To a reactor as in Example I, 800 parts by weight are introduced of a 1% aqueous chitosan solution, with properties as in Example I, along with a 0.5% solution of lactic acid. With continual agitation at 90 rpm, a 0.25% aqueous solution of potassium hydroxide is continuously introduced through a metering pump to achieve pH=6.9%. This results in the transformation of the chitosan salt from the sol form into gel. The intermediate product obtained is homogenized for 10 minutes at 1000 rpm, followed further by 1 minute of neutralization with the 0.25% aqueous potassium hydroxide solution at 4000 rpm to achieve pH=7.4. The mixture is then homogenized for 15 minutes at the same agitator speed. The product obtained is purified as in Example I.

1020 parts by wt of chitosan are obtained in form of a white, gel-like suspension with 0.75% concentration of the polymer and the following characteristics: $\overline{M}v$=398.2 kD, DD=80.6%, WRV=5200%, Pd=4.52, ash content=0.5% and average particle size in the 0.05–10 $\mu$m range.

EXAMPLE IV

To a reactor as in Example I, 900 parts by wt of a 1% aqueous solution of chitosan (with following properties $\overline{M}v$=328.2 kD, DD=82.5%, Pd=3.185 and ash content= 0.34%) are introduced along with a 0.65% aqueous salicylic acid solution. With continual agitation at 60 rpm, a 0.25% aqueous solution of sodium hydroxide is introduced continuously through a metering pump to achieve pH 5.0 to 6.9 at which pH the chitosan salt is transformed from sol to gel with partial forming of the "microcrystalline" form. The intermediate product obtained is homogenized for 2 minutes at 4000 rpm, followed by 90 seconds of neutralization with 0.25% aqueous sodium hydroxide at the same agitation speed to achieve pH=7.3. The homogenization is continued at that reaction pH=7.3 for 5 minutes. The product obtained is purified as in Example I.

445 parts by wt of chitosan are obtained in the form of a white, gel-like suspension with 2.0% concentration of polymer with the following characteristics: $\overline{M}v$=327 kD, DD=82.5%, WRV=1380%, Pd=3.05 ash content=0.05% and average agglomerate size=1–10 $\mu$m.

EXAMPLE V

To a reactor as in Example I, 1000 parts by wt of a 1% aqueous solution of chitosan (with properties as in Example I) are introduced along with a 1.5% solution of lactic acid. With continual agitation at 100 rpm, a 0.75% solution of aqueous sodium hydroxide is continuously introduced through a metering pump to achieve pH 5.0 which allows the sol/gel transition to begin. The resulting gel is agitated for 5 minutes (Trial 1) or 30 minutes (Trial 2) at 4000 rpm followed by 1 minute of neutralization with 0.75% aqueous sodium hydroxide and simultaneous homogenizing at 4000 rpm to achieve pH=7.2. The homogenization is continued for 10 minutes further at 4000 rpm. The chitosan obtained is purified as in Example I.

In both trials chitosan is obtained as a white gel-like suspension with properties as shown in Table 1 below:

TABLE 1

| Trial No | Out - put wt. parts | Concentration wt % | Mv kD | DD % | WRV % |
|---|---|---|---|---|---|
| Trial 1 | 345.0 | 2.72 | 395.4 | 80.6 | 1005 |
| Trial 2 | 350.0 | 2.75 | 277.8 | 80.6 | 1600 |

EXAMPLE VI

To a reactor as in Example I, 1000 parts by wt of a 1% aqueous solution of chitosan (properties as in Example I) are introduced along with a 1.5% solution of lactic acid. With continual agitation at 900 rpm, a 0.75% aqueous solution of sodium hydroxide is introduced through a metering pump to achieve pH 6.5 which allows the sol/gel transition. The generated gel is agitated at 4000 rpm for 5 minutes (Trial 1) and for 30 minutes (Trial 2), followed by 60 seconds of neutralization and simultaneous homogenizing at 4000 rpm to achieve pH=7.2. Under such conditions, homogenizing is continued for 10 minutes at 4000 rpm. The chitosan obtained is purified as in Example I.

The chitosan produced is in the form of a white gel-like suspension with the following properties for the two trials as shown in Table 2:

TABLE 2

| Trial No | Out - put wt. parts | Concentration wt % | Mv kD | DD % | WRV % |
|---|---|---|---|---|---|
| Trial 1 | 382.0 | 2.56 | 402.0 | 80.6 | 1240 |
| Trial 2 | 340.0 | 2.91 | 423.8 | 80.6 | 2600 |

EXAMPLE VII

A set of equipment consisting of a reactor equipped with agitator, metering pumps and a recirculation assembly with pump and an outlet for the intermediate product connected to a second reactor is used in this Example. To the first reactor, 1000 parts by wt of an aqueous solution containing 1.5% aqueous lactic acid and 1% chitosan with properties as in Example IV are introduced. With continual agitation at 1000 rpm, a 0.75% aqueous solution of sodium hydroxide is continuously introduced to achieve a pH=6.8 and to achieve the sol/gel transition. Next with the agitator running at 1000 rpm, a 1.5% solution of chitosan in lactic acid is continuously introduced with the rate of 1200 wt parts per hour. A 0.75% NaOH solution is also introduced at a rate of 585 wt parts per hour which allows the pH to be kept at 6.7–6.9. At the same time with the recirculation assembly switched on, the gel which is produced is directed to the second reactor. The gel in the second reactor is continuously neutralized to pH=7.5 to form the activated chitosan. The mixture in the second reactor is homogenized at 4000 rpm. The average retention time in the reactor is 30 minutes.

The product obtained from the second reactor is purified as in Example I. The resulting chitosan in the form of a white gel-like suspension is obtained with an output of 20 wt. parts per hour and has following characteristics: concentration= 1.94%, $\overline{M}v$=315 kD, DD=82.5%, Pd=2.95, WRV=5900%.

What is claimed:

1. A process for preparing particles of microcrystalline chitosan comprising the steps of:
    (a) forming an aqueous solution comprising at least about 0.001 percent by weight of chitosan and sufficient acid to maintain said aqueous solution at a pH that is low enough to completely dissolve said chitosan, said acid being selected from the group consisting of organic acids, inorganic acids, salts thereof, and combinations thereof;
    (b) converting said aqueous solution into a continuous gel phase having a pH ranging from about 5.0 to about 6.9 by adding a neutralizing agent while subjecting said aqueous solution to a first shear agitation;
    (c) homogenizing said continuous gel phase by applying said first shear agitation for at least about 10 seconds; and.
    (d) raising said pH of said homogenized continuous gel phase above about 6.9 with said neutralizing agent while agitating said homogenized continuous gel phase with a second shear agitation, said second shear agitation forming said homogenized continuous gel phase into a gelatinous suspension of discrete particles of microcrystalline chitosan.

2. The process of claim 1, wherein said acid is selected from the group consisting of acetic acid, lactic acid, salicylic acid, hydrochloric acid, salts thereof, and combinations thereof.

3. The process of claim 1, wherein said neutralizing agent is selected from the group consisting of sodium, potassium, ammonium hydroxide, and combinations thereof, and wherein said ammonium hydroxide comprises from about 0.01 percent by weight to about 2.0 percent by weight of said neutralizing agent in aqueous solution.

4. The process of claim 1, wherein said first shear agitation is applied at a rate ranging from about 10 sec$^{-1}$ to about 1,000 sec$^{-1}$.

5. The process of claim 1, wherein said second shear agitation is applied for a time ranging from about 1 minute to about 60 minutes at a rate ranging from about 100 sec$^{-1}$ to about 5,000 sec$^{-1}$.

6. The process of claim 1, wherein said process is a batch process.

7. The process of claim 1, wherein said process is a continuous process.

8. The process of claim 1, wherein said discrete particles of microcrystalline chitosan have a water solubility of at least about 90% at a pH of 6 after 24 hours, and wherein said discrete particles of microcrystalline chitosan have a size in the range from about 2 μm to about 20 μm.

9. The process of claim 1, wherein said chitosan of step (a) has a first water retention value, and said gelatinous suspension of discrete particles of microcrystalline chitosan has a second water retention value, and wherein said second water retention value is greater than said first water retention value.

10. The process of claim 9, wherein said second water retention value is at least about 1,000 percent.

11. A process for preparing activated chitosan particles comprising the steps of:
    (a) agitating an aqueous solution comprising from about 0.01 percent by weight to about 10.0 percent by weight of chitosan, water, and an efficacious quantity of acid, wherein said acid completely solubilizes said chitosan and lowers the pH of said aqueous solution;
    (b) removing insoluble matter from said aqueous solution by filtering;
    (c) converting said aqueous solution into a continuous gel phase having a pH ranging from about 5.0 to about 6.9 by adding a neutralizing agent and shear agitating said aqueous solution;
    (d) homogenizing said continuous gel phase by applying shear agitation for at least about 10 sec.;
    (e) raising said homogenized continuous gel phase to a pH above about 6.9 with said neutralizing agent while shear agitating said homogenized continuous gel phase;
    (f) agitating said homogenized continuous gel phase for at least about 10 seconds after said pH is above about 6.9, wherein said homogenized continuous gel phase forms a gelatinous suspension of discrete particles of activated chitosan; and,
    (g) washing said gelatinous suspension of activated chitosan particles.

12. The process of claim 11, wherein step (g) comprises washing said gelatinous suspension of activated chitosan particles with water, wherein said washing removes water-soluble salts from said gelatinous suspension.

13. The process of claim 11, wherein said acid is selected from the group consisting of acetic acid, lactic acid, salicylic acid, hydrochloric acid, salts thereof, and combinations thereof.

14. The process of claim 11, wherein said neutralizing agent is selected from the group consisting of sodium, potassium, ammonium hydroxide, and combinations thereof, and wherein said ammonium hydroxides comprise from about 0.01 percent by weight to about 2.0 percent by weight of said neutralizing agent in aqueous solution.

15. The process of claim 11, wherein said first shear agitation is applied at a rate ranging from about 10 sec$^{-1}$ to about 1,000 sec$^{-1}$.

16. The process of claim 11, wherein said second shear agitation is applied for a time ranging from about 1 minute to about 60 minutes at a rate ranging from about 100 sec$^{-1}$ to about 5,000 sec$^{-1}$.

17. The process of claim 11, wherein said process is a batch process.

18. The process of claim 11, wherein said process is a continuous process.

19. The process of claim 11, wherein said discrete particles of microcrystalline chitosan have a water solubility of at least about 90% at a pH of 6 after 24 hours, and wherein said discrete particles of microcrystalline chitosan have a size in the range from about 2 μm to about 20 μm.

20. The process of claim 11, wherein said chitosan of step (a) has a first water retention value, and said gelatinous suspension of discrete particles of microcrystalline chitosan has a second water retention value, and wherein said second water retention value is greater than said first water retention value.

21. The process of claim 20, wherein said second water retention value is at least about 1,000 percent.

* * * * *

UNITED STATES PATENT AND TRADEMARK OFFICE
CERTIFICATE OF CORRECTION

PATENT NO. : 6,740,752 B2
DATED : May 25, 2004
INVENTOR(S) : Struszcyk et al.

It is certified that error appears in the above-identified patent and that said Letters Patent is hereby corrected as shown below:

Title page,
Item [*] Notice, should read: -- Subject to any disclaimer, the term of this patent is extended or adjusted under 35 U.S.C. §154(b) by 0 days.

This patent is subject to a terminal disclaimer. --

Signed and Sealed this

Fifteenth Day of February, 2005

JON W. DUDAS
*Director of the United States Patent and Trademark Office*